United States Patent [19]
Jones

[11] 3,941,122
[45] Mar. 2, 1976

[54] HIGH FREQUENCY ULTRASONIC PROCESS AND APPARATUS FOR SELECTIVELY DISSOLVING AND REMOVING UNWANTED SOLID AND SEMI-SOLID MATERIALS AND THE LIKE

[75] Inventor: Joie P. Jones, Sherborn, Mass.

[73] Assignee: Bolt Beranek and Newman, Inc., Cambridge, Mass.

[22] Filed: Apr. 8, 1974

[21] Appl. No.: 458,793

[52] U.S. Cl. ............................................. 128/24 A
[51] Int. Cl.² ................... A61H 23/00; A61B 17/00
[58] Field of Search ....:........................... 128/24 A

[56] References Cited
UNITED STATES PATENTS

| | | | |
|---|---|---|---|
| 3,565,062 | 2/1971 | Kuris | 128/24 A |
| 3,589,363 | 6/1971 | Banko et al. | 128/24 A X |
| 3,721,227 | 3/1973 | Larson et al. | 128/24 A X |

OTHER PUBLICATIONS

Baum, Gilbert et al., "The Application of Ultrasonic Locating Techniques to Ophthalmology", IN Am. Jour. Ophth. 465, Part II; 319-329: Nov. 1958.

*Primary Examiner*—Channing L. Pace
*Attorney, Agent, or Firm*—Rines and Rines

[57] ABSTRACT

The present disclosure deals with ultrasonically selectively dissolving solid and semi-solid unwanted materials, such as vitreous gels, membranes, cataracts and similar materials in ophthalmic operation applications, for example, by radiating from a physically small source, high-frequency, preferably pulsed, acoustic waves, while positioning the material to be selectively locally dissolved by such waves at a selected region sometimes in contact with or near-contact or within a short distance from the source of the order of a millimeter or so, at which the propagated acoustic wave energy can effect such phenomena as, for example, localized cytolysis of the material at the selected region thereof substantially normal to the wavefront of the radiated acoustic wave region, and without substantial damage to the portions of the material external to said selected region, and with adjustment to obviate any substantial temperature rise at the material.

26 Claims, 1 Drawing Figure

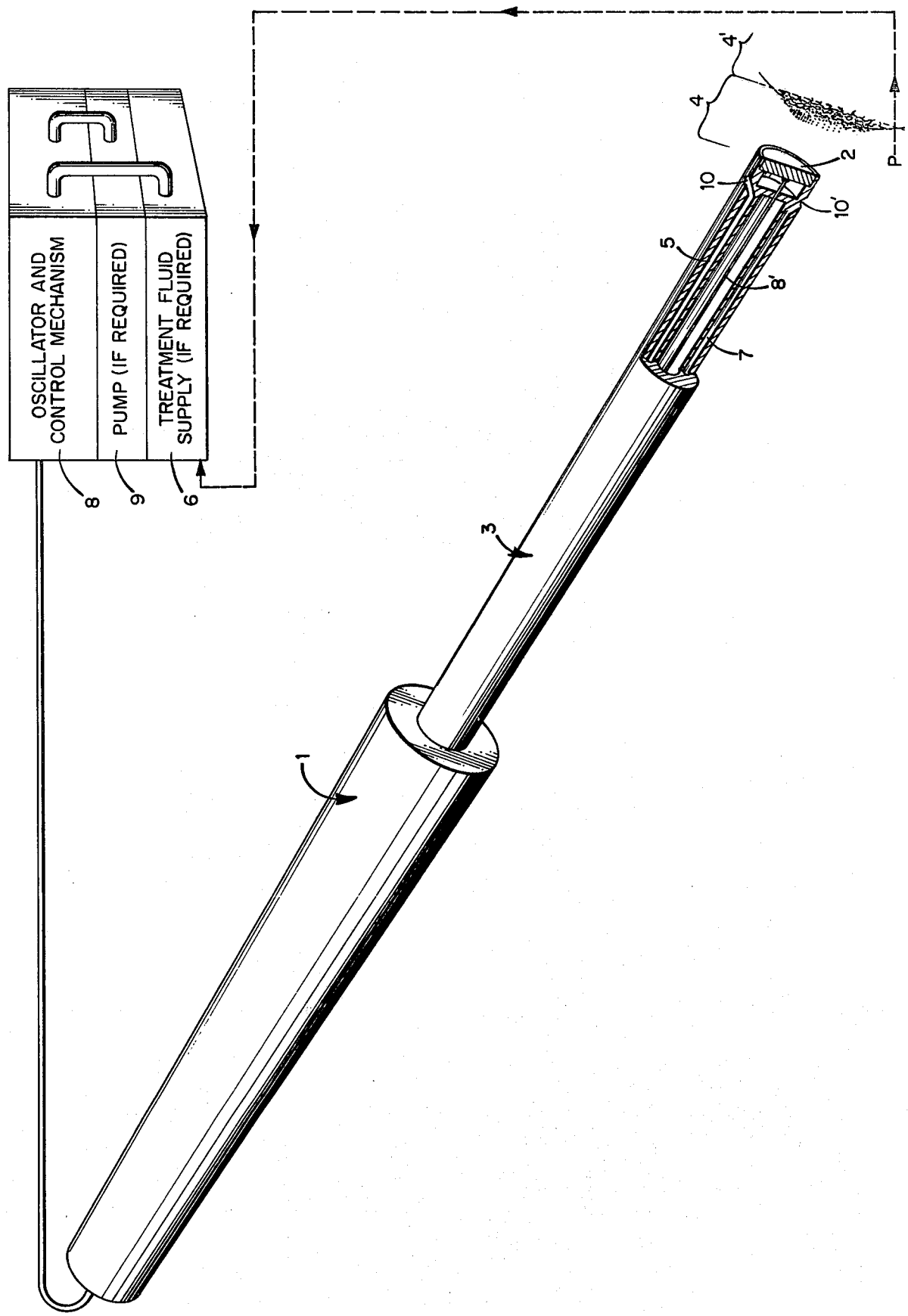

HIGH FREQUENCY ULTRASONIC PROCESS AND APPARATUS FOR SELECTIVELY DISSOLVING AND REMOVING UNWANTED SOLID AND SEMI-SOLID MATERIALS AND THE LIKE

The present invention relates to processes and apparatus for selectively ultrasonically dissolving and removing unwanted solid and semi-solid materials and the like, having an important, though by no means exclusive, application in procedures for the removal of vitreous gels, membranes, cataracts and the like in ophthalmic operations, as well as important use in other parts of the human and animal bodies including, but not limited to, kidney stones and the like, tissue, abscesses, tumors, arterial deposits and the like; and, indeed, in a wide variety of other unrelated applications, including industrial processes, wherein materials are desired to be selectively dissolved (liquified) in a very localized region.

In view of its importance, accordingly, the invention will hereinafter be primarily described for purposes of illustration in connection with its application to such ophthalmic and related procedures; but it is to be distinctly understood that this is by way of illustration only, and that the invention has obviously much broader and wider applications, as well, wherever the advantages thereof are sought, as more particularly delineated in the appended claims.

The art is replete, as hereinafter detailed, with prior proposals for uses of relatively low ultrasonic frequency energy for a wide variety of purposes ranging from communications to polishing, and including the particularizing of materials, even for ophthalmic and related applications. Particularly with regard to the latter applications, however, such uses have had disadvantages preventing them from being completely satisfactory. The novel relatively high frequency ultrasonic technique for dissolving and removing unwanted material of the present invention, on the other hand, is especially suitable for surgical procedures where the total disintegration of vitreous gel, vitreous membrane, lens, lens capsule and cataract, and like materials is desired without the disadvantage of prior art proposals that produce suspensions of particularized material that must be physically taken away from the surgical site. The technique makes use of a small, high frequency ultrasonic transducer driven at acoustical power levels rather critically selected, in conjunction with the operating frequencies, so that dissolving only occurs in close proximity to the face of the transducer. Adverse rises in temperature are prevented preferably by selecting a particular pulsed mode of operation (though in some particular instances continuous wave operation and/or cooling may be necessary), such that coagulation of tissue, including rendering the material in the eye opaque, causing at least temporary loss of vision, and other disadvantageous effects accompanying adverse temperature rises can be avoided. Whereas state-of-the-art techniques use relatively low frequency ultrasonic vibrating assemblies which are employed to break apart unwanted material by mechanical impact or cutting action, the present technique uses a radiated propagating pulse of relatively high frequency ultrasonic energy to convert or dissolve unwanted material into its cellular, subcellular and/or molecular components in a highly controlled and localized manner.

Vibratory assemblies for cutting material have been used for some time in a wide number of applications. One such apparatus employs a slurry of abrasive particles in conjunction with an ultrasonically vibrating tool, as described, for example, in U.S. Pat. No. 2,580,716. The vibratory energy imparted to the abrasive particles in the slurry hurls them with tremendous accelerations against the surface to be cut, thereby literally chipping away the material. This technique has been applied with great success particularly in the case of industrial machine tools. Such vibratory assemblies, however, are ineffective in cutting yielding materials and also require a fairly open site so that the interposition of the slurry between the vibrating tool tip and the work surface can be maintained.

Certain vibratory assemblies for particular use in the dental field do not necessarily require the use of an abrasive slurry to break down unwanted material. Such assemblies are described, for example, in U.S. Pat. Nos. 3,075,288; 3,076,904; and 3,213,537. Since these instruments rely on the mechanical action of a vibrating tool to break down unwanted material, they do not operate on the principle of the present invention, or produce the novel results thereof. Since, moreover, these dental instruments generally break down material into relatively large particles and generally do not provide for the removal of unwanted material, they are inappropriate for use in inaccessible places.

U.S. Pat. No. 3,589,363, on the other hand, does describe a vibratory assembly for material removal from relatively inaccessible regions. This instrument uses a rapidly vibrating knife tip to break down unwanted material into small particles. As the vibrating tip is applied to the material, the region adjacent to the operative site is flooded with fluid. The unwanted material is dispersed into the fluid which, in turn, is removed by suction. Although the vibrating tip will, as a result of this motion, produce an acoustic wave which propagates into the unwanted material, it is clearly the cutting motion of the tip and not the propagation of radiated acoustic energy which produces the desired action and result. (See, for example, C. D. Kelman, "A Personal Interview Between the Editor and Dr. Charles D. Kelman," *Boyd's Highlights of Ophthalmology*, Volume XIII, No. 1, 1970–71 Series, p. 43.) Thus, such devices do not operate on the principle of the present invention. Such prior art devices also cannot attain the novel controlled results of this invention as more fully hereinafter explained.

The device described in U.S. Pat. No. 3,589,363 illustrates a prior proposal designed particularly for ophthalmic applications. One of its disadvantages is that suction is required as before-mentioned not only to remove unwanted material, but actually to hold the material while the vibrating tip chips away at or cuts it because of dependence on mechanical action as opposed to the dissolution of material by this invention without or with slight physical contact. Kelman, who invented and developed the device, and others have found that the instrument will not break down the lens capsule and that this material must be removed by conventional cutting and manipulation with forceps. (See C. D. Kelman, "Phakoemulsification and Aspiration, A New Technique for Cataract Removal: A Preliminary Report", *Am. J. of Oph.* 64 (1967), pp. 23–35; C. D. Kelman, "Phakoemulsification and Aspiration," *Am. J. of Oph.* 67 (1969), pp. 464–477; and C. D. Kelman and D. L. Brooks, "Ultrasonic Emulsification and Aspiration of Trasematic Hyphema," *Am. J. of Oph.* 71, (1971), pp. 1289–1291).

In the procedure used by Kelman the anterior lens capsule has to be first torn away with a very dull knife, and then the knife is removed from the eye. Next, a spatula is inserted to pro-lapse the lens cortex to the anterior chamber; that is, one must go in with a spatula and scrape out the lens material into the anterior chamber of the eye. The spatula is then removed; and finally the probe is placed inside the eye and used to break down and remove the lens material after which the probe is removed. If the back side of the lens or the posterior capsule is still rather opaque, one must insert a knife into the eye again to cut the posterior capsule. In accordance with the present invention, however, rather than going through four such rather complicated stages in which four different instruments must be inserted into the eye, this invention allows the surgical procedure to be performed, in many instances, with only one instrument.

Several workers have investigated the effects of certain ways of using ultrasonic energy directly, rather than through a vibrating assembly and/or an abrasive slurry, to break apart unwanted material. The exploration of ultrasonics as a therapeutic tool in ophthalmology was apparently begun by Zeiss, (E. Zeiss, "Uber Linsenueranderungen An Heraus Genommenen Rinderlinsen durch Ultra-schallein Wirkung," *Arch. F. Ophth.* 139 (1938), pp. 301–322), who noted that 250 kHz acoustic energy deleterously produced reversible perinuclear cataracts and vitreous flow in excised beef eyes. Kawamoto, (I. Kawamoto, "Experimental Studies on the Effect of Ultrasonic Waves on the Eyeball", *Nippon Gankwa Gakukwai Zasshi*, 51 (1947), pp. 12–16), obtained similar results working at 547 kHz. Lavine, (O. Lavine, K. H. Langenstrass, C. M. Bowyer, F. E. Fox, V. Griffing, and W. Thaler, "Effects of Ultrasonic Waves on the Refractive Media of the Eye," *Arch. Ophth.* 47 (1952), pp. 204–219), used frequencies ranging from 0.5 to 3.2 MHz and developed dense irreversible cataracts under experimental conditions. Baum, (G. Baum, "The Effect of Ultrasonic Radiation Upon the Eye and Ocular Adnexa," *Am. J. of Oph.*, 42 (1956), pp. 696–706), noted that 1 MHz energy applied to the rabbit eye caused significant iritis and ciliary body injury. Donn, (A. Donn, "Ultrasonic Wave Liquefaction of Vitreous in Living Rabbits," *Arch. Oph.*, 53 (1955), pp. 215–223), broke up vitreous in the rabbit eye with focused ultrasound, but created retinal changes which were not visible ophthalmoscopically but which were quite apparent histologically. While Karlin, (D. B. Karlin, "Ultrasound in Retinal Detachment Surgery," *Trans. Am. Acad. Oph. and Otolaryng.* 73 (1969), pp. 1061–1076), found that ultrasound in the kHz frequency range could be used to produce particularization in blood-injected cattle vitreous, Letts and Rosen (N. F. Letts and A. Rosen, "The Destruction of Vitreous and Retina with a 40 kHz Ultrasonic Probe Introduced Into the Living Rabbit Eye," to be published in *Trans. Am. Acad. Oph. and Otolaryng.*), extended these experiments into living rabbit eyes and found that deleterous retinal and choroidal hole formation occurred at the energy levels required for vitreous liquefaction. Vitreous membranes, moreover, could not be destroyed by this method.

Apparently none of this myriad of prior investigators understood or discovered the phenomena underlying the present invention that, for the first time, enable the direct harnessing of radiated acoustic energy for therapeutic purposes in ophthalmology and other areas, and, through the entirely different and critical technique for developing, adjusting and using radiated acoustic energy underlying the invention, turning an unsuccesssful and even dangerous technology into a highly controllable, predictable, repeatable, localized, safe and simplified technique.

One of the novel features of this invention occurs on the fact that prior-art attempts in dissolving material, and in particular cytolysis or the like of unwanted tissue and the like, resulted in extremely low attenuation of various forms of energy, thereby preventing control and localization. The relatively low ultrasonic frequencies that were used traveled much farther before being substantially attenuated than the relatively high ultrasound frequency waves of this invention. The low-frequency ultrasound resulted, indeed, in energy conversion to heat, physical forces, and acoustic pressures over an undesirably large area, as opposed to confining the energy in the unwanted material or tissue. Furthermore, to compound the low attenuation problems encountered, previous investigators used continuous ultrasonic frequency waves under the theory that it was necessary to break down the material in as short a time period as possible.

In accordance with a preferred form of the present invention, by contrast, very short wave-length ultrasonic waves are employed which do not travel far because of the correspondingly high ultrasonic frequency associated therewith. It has been found that such high-frequency ultrasonic energy is highly attenuated over a short distance due to various energy transfer mechanisms at the molecular and macromolecular levels. It is believed that the reason for this high-energy absorption in the immediate region of the source and the ability of the technique to effectively break down materials is due to the fact that these high-frequency waves are extremely close to the average resonant frequency of cell structures and macromolecules whose dimensions are in the same range as the small wavelength associated with the high-frequency ultrasound underlying the inventive technique. Thus, e.g. cells and components thereof are put into a vibrational phase resulting in various types of shear and torsional stresses causing intracellular or molecular bonds to break apart. In essence, an important distinction over the prior art is that this invention transmits energy to unwanted material in a controllable, localized area in such a manner that both the unwanted material and the ultrasonic source become active elements in the vibratory dissolving process. This is significantly different from the prior art where only the ultrasonic source is active while the undesirable material remains a passive element to be broken up by physical contact and forces generated by the working surface of the ultrasonic probe. Since this invention, furthermore, does not depend upon physical contact force, it has been found, directly contrary to the prior art, that stimulating the undesirable material or tissue with pulsed ultrasound energy will actually reduce disintegration time because substantially higher energy amplitudes, hence energy densities, can now be applied intermittently to the undesirable material with the assurance that there will be in high attentuation due to energy absorption of the high-frequency vibratory mode of the undesirable material between the programmed relatively long time gaps of no energy stimulation.

Apart from the fact, shown above, that prior skilled investigators failed to discover the present invention and, indeed, by their different techniques obtained unsuccessful and useless results insofar as several of the purposes of the invention are concerned, the whole understanding (or what now proves to be lack of understanding) of the mechanisms involved and the resulting teachings in this art, clearly led investigators away from the discoveries underlying the invention. Thus, for example, Baum, supra, found that for continuous exposure times of less than six minutes, the acoustic power levels which will always produce permanent damage to the eye are only 4dB above the acoustic power levels which can always be considered safe. Using experimentally determined values for the attenuation of sound in the eye, Baum's study, (P. N. T. Wells, *Physical Principles of Ultrasonic Diagnosis*, Academic Press, 1969, pp. 19–27), implies that if the power applied to a 1 MHz transducer is increased until liquefaction is just observed at the transducer's face, then the acoustic energy which propagates into the eye will not be attenuated to a safe level until it has traveled a distance of 40 cm. The effects of attenuation are even more dramatic at lower frequencies. For example, if 40 kHz acoustic energy (as distinguished from a mechanical knife moving at 40 kHz) is used to break down material in the eye, the wave must propagate over 10 meters before the wave's intensity is attenuated to a level which can be considered absolutely safe. Thus, unless expensive and complicated apparatus is used to focus the acoustical energy down to a small region, it is impossible to use low frequency ultrasound (having a frequency below a few MHz) safely to liquefy material in the eye without damaging surrounding tissue.

An object of the invention, accordingly, is to provide a new and improved process and apparatus for employing high-frequency ultrasound acoustic wave energy at very high density, preferably intermittently, to dissolve materials, particularly semi-solid and solid materials, which process and apparatus shall not be subject to the above-recounted and other disadvantages and problems of prior techniques, but that, to the contrary, produce highly controllable, selective and localized tissue reduction results and without damage to surrounding material.

A further object is to provide such a novel process and apparatus that is particularly adapted and safe for ophthalmic procedures and for other procedures on the human or animal body and with the above novel results.

An additional object is to provide an improved selective ultrasonic dissolving and removing process and apparatus of wide and flexible application, generally applicable to unwanted or other solid and semi-solid materials and the like to be dissolved or removed.

Other and further objects will be explained hereinafter and are more particularly defined in the appended claims. In summary, however, from one of its broad aspects, the invention embraces a process for selectively dissolving solid and semi-solid materials, that comprises, producing preferably pulsed ultrasonic frequency energy; propagating such energy as a radiated acoustic wave from a predetermined, preferably highly localized, region; positioning the material-to-be-dissolved, of dimensions large compared with the wavelength of said ultrasonic frequency, at a juxtaposed region thereof, in contact, near-contact or slightly displaced therefrom, to subject the material to the propagated acoustic wave energy; adjusting the energy to effect localized dissolving of the material into cellular components at said juxtaposed region thereof substantially normal to the wavefront of the acoustic wave while rapidly attenuating the energy to prevent dissolving and other substantial damage to the portions of the material external to said juxtaposed region. Where pulsing of the energy is employed, such is adjusted to obviate any substantial temperature rise in the material, and said frequency is selected to produce the desired degree of localization and disintegration of the resulting dissolved material.

The invention will now be described with reference to the accompanying drawing, the single FIGURE of which is a partly schematic and isometric drawing illustrating the invention as applied to an ophthalmic or similar instrument or tool for the purposes of the invention.

As before indicated, the present invention involves high ultrasound frequencies. For certain ophthalmic applications, frequencies of the order of 90 to 100 MHz and higher have been found particularly useful for reasons later apparent. The attenuation of ultrasound in the eye in such high MHz ranges has been determined to be approximately proportional to the 1.3 power of frequency. It follows that if a 100 MHz sound wave is just intense enough to dissolve material in the eye, the wave need propagate only 1 mm for the effects of attenuation to reduce the intensity of the wave to what can be considered to be a safe level. This analysis indicated that ultrasound having a frequency in the 100 MHz range could be used to dissolve unwanted material in a very localized region without deleteriously affecting the surrounding tissue. The physical mechanisms which describe the breakdown of material are found to be frequency-dependent. Thus, when the wavelength of sound is larger than or about the same size as the physical dimensions of the eye, cavitation and/or gross mechanical motion produce the break-up of unwanted material. Such a situation certainly exists if the frequency of the sound is around 40 kHz or below, as in certain prior-art systems before-discussed. When, however, the wavelength of sound is very much smaller that the dimensions of the eye or its parts — as it is at 100 MHz — then the mechanical energy associated with the propagating sound wave will microscopically break down the unwanted material into cellular macromolecular, and/or molecular components. This process is best described as one of cytolysis since the sound energy breaks down the materials into a subcellular or cellular collection of particles. Because the attenuation is frequency-dependent, the selected region over which liquefaction occurs is also frequency-dependent. Thus, liquefaction can be localized to a region of arbitrary size; and since the degree of material breakdown is frequency-dependent, the unwanted material can be dissolved on a micromolecular level of arbitrarily desired dimensions. These unique features are not possible with those previous techniques which depend on a vibrating mechanical tool, an abrasive slurry, cavitation phenomena, and/or the focusing of acoustical energy.

The above has, indeed, been confirmed by a series of in vitro experiments in which 90 MHz pulsed ultrasound was applied successfully, for the purposes of the invention, to lens, cataract, vitreous, and vitreous membrane in excised human, cattle, baboon, and rabbit material. A generator was used to drive a resonant frequency PZT crystal at its first overtone of 90 MHz. The pulse length was about 1 $\mu$sec and the pulse repetition rate about 100 per second. The biological sample was held with forceps and subjected to the active surface of the transducer. The power was slowly increased until dissolving or cytolysis was observed at the face of the transducer. In all tests, dissolving or cytolysis appeared to be localized to a region normal or perpendicular to and within 1 mm of the transducer's face. Ultrasound was found to dissolve all materials tested including lens, cataract, vitreous, and vitreous membrane. A small thermocouple was placed at various positions within most of the samples tested. Only small variations in temperature were recorded during liquefaction. At a distance of about 2 mm from the transducer surface, the maximum rise in temperature was only 1°C.

The accompanying drawing illustrates a practical device, incorporating the aforementioned principles of dissolution using high-frequency ultrasonic energy, this particular instrument lending itself to the performance of delicate surgical procedures in extremely limited regions. This device is capable of liquefying lens, cataract, vitreous and vitreous membrane with no significant temperature rise and with no damage to peripherally surrounding tissue; and, of course, may also be used for a host of other applications, as before suggested, including other operations upon the body or upon other kinds of solid and semi-solid materials and the like that are to be dissolved and removed.

In brief, the device shown in the drawing consists of a casing 1 in which is mounted a transducer 2, should as a piezoelectric disc mounted as a small tip-like source at the end of a probe construction 3 for converting electrical energy into ultrasonic energy, piezoelectrically, as before discussed. The ultrasonic energy propagates into the unwanted material 4–4' and causes the unwanted material to dissolve more particularly indicated at 4. Although in many circumstances material will have been dissolved at 4 to a degree such that it need not be physically removed from the surgical site (an advantage lacking in the prior) art, there are applications wherein the removal of the unwanted material may be desirable. For this latter case, the casing 1 in which the transducer 2 is mounted can be modified, as shown in FIG. 1, to include a lateral longitudinal passage 5 in the probe 3 for carrying treatment fluid from a fluid supply 6 through outlet 10, disposed just peripherally rearward of the transducer 2, to the adjacent region where ultrasound is applied; and a similar longitudinal passage 7 for carrying unwanted dissolved material in the treatment fluid away from the first region, under suction. The apparatus also includes an oscillator or generator 8 for supplying electrical energy via conductors 80', shown centrally axially mounted, to the transducer 2; and, where desired, the fluid supply source 6 is used for providing treatment fluid, and suction pump means 9 is provided for withdrawing the fluid at 10', adjacent the transducer 2, when the fluid contains a suspension of unwanted material. As the operative tip 2 is applied to the material 4–4', the region adjacent to the operative side can thus be bathed with the treatment fluid. The unwanted material will then naturally run out of the incision, or suction at 10'–9 can enable withdrawing the material from the operative site.

In operation, pulsed high-frequency ultrasonic energy is applied from oscillator 8 to the transducer 2 so as to produce an ultrasonic impulse wave which propagates into the unwanted material 4–4'. The ultrasonic frequency and power level are selected, based on a knowledge of the acoustical properties of the material, so as to limit dissolving or cytolysis to a specified region; and the pulse length and pulse repetition rate are selected so as to minimize any changes in temperature produced by the ultrasonic wave, as before explained. For example, in many ophthalmic applications, it will be beneficial to use an ultrasonic oscillator frequency of about 100 MHz, a pulse length adjusted to about $1\mu sec$ (microsecond) or a few $\mu sec$, and a pulse repetition rate adjusted to about 100 per second or a few hundred. These parameters will enable the dissolving or cytolysis process to be localized to the region 4 within about 1 mm of the surface of the transducer, with pulse power on the order of several watts/cm². The radiating tip 2 may have a cross-dimension on the order of about 10 to 100 times the wavelength. Unwanted material dissolving in the micron range is produced for example, with about 100 MHz frequencies.

In employing the instrument illustrated, the surgeon maniuplates the casing handpiece 1 to apply the radiating tip 2, extending beyond the hand-holding region, at the selected juxtaposed regions spaced very short distances from the tip, such as a millimeter or a few millimeters, where the pulses of radiated acoustic wave energy introduce no substantial temperature rise. The resulting attenuation is controlled for the localized cytolysis with the dissolved material 4 flushed away in the flow of the treating fluid. Beyond 4 at 4', the ultrasonic energy has attenuated to a degree such that no dissolving action takes place. This process continues until all of the unwanted tissue has been dissolved and, if necessary, removed from the operative site. As before stated, moreover, in accordance with the invention, dissolving or cytolysis is highly localized and controllable to prevent damage at peripheral regions of the material. It may also be desirable to aspirate the unwanted material out of the wound hole itself so that another passage in the probe to carry out the material may not be needed. The size of the wound hole would be large enough to provide adequate irrigation through a tube, not shown, affixed to the probe and large enough to provide adequate aspiration from the eye around the probe, but yet small enough to enable the surgeon to maintain appropriate pressure in the eye. Note the latter consideration (re maintenance of pressure) is an important factor in ophthalmic applications.

Where fluid treatment has been employed in the before-discussed prior-art chipping devices, the treatment fluid serves to cool the tip of the probe, to wash material out of the eye, and to remove such material. The eye is not inflated during all stages of the operating using such devices, even though surgeons prefer to have the eye inflated at all times. In accordance with the present invention, on the other hand, the treatment fluid, if employed, may be primarily used to keep the eye inflated, as by letting saline solution run into the eye by gravity, selecting the diameter of the irrigation tube and the wound size (used for aspiration) so that the specified pressure range is maintained. A very small pressure-sensitive monitor transducer P may also be employed, carried by the probe 3, if desired, directly to measure the pressure in the eye, as at 4, and then regulate the flow of fluid from 6 into the eye by well-known feedback control, schematically indicated by the arrows adjacent P and the supply 6.

Clearly this technique and type of apparatus may be used, also, for other applications, as previously discussed; also, with, for example, piston-type, spherical and cylindrical sources employing appropriate frequencies, as before explained; and further modifications will also occur to those skilled in this art--all such being considered as falling within the spirit and scope of the invention as defined in the appended claims.

What is claimed is:

1. A process for selectively dissolving solid and semi-solid materials, comprising producing ultrasonic-frequency energy of the order of at least 90–100 Mhz, propagating such energy as a radiated acoustic wave from a predetermined region and upon material-to-be dissolved at a juxtaposed region to subject the material to the radiated acoustic wave energy and thereby dissolve the material locally into cellular components at said juxtaposed region thereof substantially normal to the wavefront of the acoustic wave and rapidly attenuating the energy in the material at said juxtaposed region to prevent dissolving and other substantial damage to the portions of the material external to said juxtaposed region and to prevent any substantial temperature rise external to said juxtaposed region.

2. A process as claimed in claim 1 and in which the said energy producing comprising producing pulses of ultrasonic-frequency energy.

3. A process as claimed in claim 2 and in which said energy producing comprises producing pulses of the order of microseconds long and of repetition rate of the order hundreds per second.

4. A process as claimed in claim 1 and in which said predetermined region is positioned so as to be located a short distance from said juxtaposed region.

5. A process as claimed in claim 1 and in which said predetermined region is positioned so as to be located a distance of the order of millimeters from said predetermined region.

6. A process as claimed in claim 1 and in which said propagating comprises propagating said energy upon at least a portion of a human or animal eye.

7. A process as claimed in claim 6 and in which said energy producing comprises producing pulses of ultrasonic-frequency of the order of one to a few microseconds long and having a repetition rate of the order of one to a few hundred per second.

8. A process as claimed in claim 7 and in which said predetermined region is positioned so as to be located a distance of the order of a millimeter from said juxtaposed region.

9. A process as claimed in claim 8 further comprising injecting treating fluid into said juxtaposed region and withdrawing said fluid therefrom to carry off dissolved material.

10. A process as claimed in claim 1 further comprising injecting treating fluid into said juxtaposed region and withdrawing said fluid therefrom to carry off dissolved material.

11. A process as claimed in claim 10 further comprising measuring the pressure of the material at said juxtaposed region and controlling said injecting in accordance with said measuring.

12. A process as claimed in claim 1 and in which said energy producing comprises producing ultrasonic-frequency energy of wavelength corresponding to the dimensions of said cellular components and small compared to the dimensions of said material.

13. A process for dissolving solid and semi-solid materials, comprising the steps of producing ultrasonic-frequency energy of the order of at least 90–100 Mhz; and transmitting said energy through a predetermined volume of material to be liquefied and thereby directly converting said energy simultaneously with said transmitting step into stress on a macromolecular and cellular level in said volume of material and dissolving said volume of material into macromolecular size components.

14. The process of claim 13, wherein said energy producing comprises generating pulses of said energy of duration, repetition rate, and frequency within predetermined ranges dependent upon the dimensions of said volume and type of said material.

15. The process of claim 13, wherein said dissolving comprises permanently rupturing adjacent macromolecular component bonds.

16. The process of claim 13, wherein said energy producing comprises producing ultrasonic-frequency acoustic energy of wavelength approximately the same as the dimensions of macromolecules and cellular components in said volume of material to be stressed and wherein said converting comprises vibrating said volume of material on a macromolecular level.

17. Apparatus for selectively dissolving solid and semi-solid materials, having, in combination, means for generating ultrasonic-frequency energy of the order of at least 90–100 Mhz; transducer means connected with the generating means and dimensioned to comprise a highly localized acoustic-wave radiating tip; casing means containing said radiating tip and shaped to enable manual manipulation thereof in order to enable application of said radiating tip to juxtaposed region of such materials to propagate therein the radiated acoustic waves for producing a localized dissolving of the materials substantially normal to the wavefront and immediately at said juxtaposed region and thereby to attenuate the waves rapidly in the materials at the juxtaposed region, to prevent dissolving and other substantial damage to the portions of the materials external to said juxtaposed region and to prevent substantial temperature rise of said materials external to said juxtaposed region; and means for setting said frequency to control the size of the resulting dissolved components of the material.

18. Apparatus as claimed in claim 17 and in which means is further provided for introducing treating fluid to the said juxtaposed region and for withdrawing the same therefrom to carry off dissolved material.

19. Apparatus as claimed in claim 18 and in which said generating means comprises means for producing pulses of the order of microseconds at repetition rate of the order of hundreds per second.

20. Apparatus as claimed in claim 19 and in which said juxtaposed region is at a distance of the order of millimeters from said radiating tip.

21. Apparatus as claimed in claim 17 adapted for opthalmic and similar operations and in which said radiating tip extends from its casing means to enable positioning of the tip very close to selected regions of the eye and the like.

22. Apparatus as claimed in claim 21 and in which means is further provided for introducing treating fluid into said juxtaposed region and for withdrawing the same therefrom to carry off dissolved material.

23. Apparatus as claimed in claim 22 and in which means is provided for measuring the pressure at said juxtaposed region and for correspondingly controlling the introduced fluid.

24. Apparatus as claimed in claim 21 and in which said generating means comprises means for producing microsecond pulses of the order of one to a few hundred per second.

25. Apparatus as claimed in claim 24 and in which said juxtaposed region is at a distance of the order of a millimeter from said radiating tip.

26. Apparatus as claimed in claim 22 and in which said transducer means comprises a radiating surface disposed at the end of a cylindrical probe extension of said casing means, and said fluid introducing and withdrawing means comprise passages extending longitudinally along said probe and opening peripherally near said end.

* * * * *